United States Patent [19]
Macho et al.

[11] Patent Number: 5,451,350
[45] Date of Patent: Sep. 19, 1995

[54] TEST CARRIER FOR THE DETERMINATION OF AN ANALYTE AS WELL AS A PROCESS FOR ITS PRODUCTION

[75] Inventors: Heinz Macho, Fuerth-Fahrenbach; Rolf Lerch, Ilvesheim; Herbert Harttig, Altrip; Volker Zimmer, Ludwigshafen-Edigheim, all of Germany

[73] Assignee: Boehringer Mannheim GmbH, Mannheim, Germany

[21] Appl. No.: 68,110

[22] Filed: May 28, 1993

[30] Foreign Application Priority Data

May 29, 1992 [DE] Germany ............... 42 17 733.2

[51] Int. Cl.⁶ ............................................. G01N 1/18
[52] U.S. Cl. ........................... 264/442; 264/321; 264/325; 264/327; 422/56; 422/58; 422/86; 436/164; 436/810; 435/4; 435/805; 427/2.11; 427/2.13
[58] Field of Search .................... 422/55–60, 422/61, 82.05, 82.09, 86; 436/164, 165, 169, 805, 810; 435/4, 291, 805, 808; 424/7.1; 427/2; 264/23, 25, 321, 325, 327

[56] References Cited

U.S. PATENT DOCUMENTS

| 4,235,601 | 11/1980 | Deutsch et al. | |
|---|---|---|---|
| 4,678,757 | 7/1987 | Rapkin et al. | 436/169 |
| 4,837,373 | 6/1989 | Gunkel et al. | 422/56 |

FOREIGN PATENT DOCUMENTS

| 0126357A1 | 11/1984 | European Pat. Off. |
| 0133895 | 3/1985 | European Pat. Off. |
| 0166365 | 1/1986 | European Pat. Off. |
| 0185982 | 7/1986 | European Pat. Off. |
| 0199205A1 | 10/1986 | European Pat. Off. |
| 0209032 | 1/1987 | European Pat. Off. |
| 0443231A1 | 8/1991 | European Pat. Off. |
| 2934760 | 3/1980 | Germany. |
| 3222366A1 | 12/1982 | Germany. |
| 3442820A1 | 6/1985 | Germany. |

Primary Examiner—David A. Redding
Attorney, Agent, or Firm—Nikaido, Marmelstein, Murray & Oram

[57] ABSTRACT

An analytical device determines the analytes in a liquid sample. This device includes a layer of flat material which has a sample application area and a detection area thereupon. The detection area includes a reagent for determining the analyte, and the absorbent sample application area and the absorbent detection area are disposed within a liquid impermeable boundary. The layer of flat material also includes an absorbent connector which is disposed such that the sample application area and the detection area are connected by the absorbent connector. The liquid impermeable boundary and the absorbent connector prevents liquid from being transported between the sample application area and the detection area, except through the absorbent connector.

85 Claims, 5 Drawing Sheets

TEST CARRIER FOR THE DETERMINATION OF AN ANALYTE AS WELL AS A PROCESS FOR ITS PRODUCTION

The invention concerns test carriers for the determination of an analyte with thermally generated boundaries which are used to direct a stream of liquid in an absorbent material from a sample application zone to a detection zone whereby the sample liquid cannot be transported through the boundaries. In addition the invention concerns a process for the production of such a test carrier.

Test carriers are understood as analytical devices in which the reagents necessary for carrying out the determination of a sample component are present in or on solid materials. Such carrier materials can generally be absorbent fibrous or porous materials, or materials capable of swelling, such as fleeces, tissues, membranes or film-like materials. Paper is for example a common absorbent carrier material. The carrier materials themselves can be rigid and thus self-supporting or they can also be mounted on a rigid support such as one made of plastic. Since the reagents necessary for the determination of an analyte in test carriers are located on or in dry reagent carrier materials for example in a coated or impregnated form, determinations are often also denoted dry-chemical tests as an allusion to the form in which the reagents are used. Test carriers are known to a person skilled in the art in various forms for example as strips, square slides etc.

In the U.S. Pat. No. 4,235,601 Deutsch et al. describe test carriers which are present as single-layered dipstick tests. Reagents are impregnated at certain sites on paper. If, after sample application, such a strip of paper is placed in chromatographic liquid the sample together with the migrating liquid comes into successive contact with the reagents located on the paper. The different chromatographic properties of the product derived from the analyte to be detected and reagent, of the excess reagent as well as of those by-products and sample components which are not of interest finally enables the analyte in the sample to be examined to be determined at a certain site on the test strip. In order that the differences in chromatographic properties, which are often only slight, may be brought into effect relatively long chromatographic paths are necessary. This is associated with a relatively high liquid requirement in order to enable migration through all the zones of the test carrier.

In general less liquid is required for multilayered test carriers in which the individual layers are positioned on top of one another and fulfil different functions. Thus such test carriers can for example comprise a distribution layer, reagent layer(s), possibly an optical barrier layer, a carrier layer etc. Such test carriers are for example known from DE-A 3222366 or EP-A 0 166365.

A liquid sample is applied to the uppermost layer and in doing so diffuses laterally as well as downwards. It is advantageous to moisten the entire layer material. When the analyte reacts with the reagents present in one or several layers a colour is usually formed or changed. This colour formation or change in colour is an indication of the presence of the analyte to be determined and can be observed visually or be measured quantitatively by means of photometry and can thus be utilized for the quantitative determination of an analyte.

Multilayer reagent carriers are described in DE-A 2934760 which should be suitable for carrying out different analyses simultaneously. For this a so-called "integrated material" is proposed which has three or more "reagent layer units" on one carrier as well as a porous spreading or distribution layer. The respective reagent layer units contain reagents for various chemical analyses. They are arranged on a carrier layer in such a way that approximately the same proportions of which are located within a distribution circle defined by the diffusion of a liquid sample when it passes through the porous distribution layer. The entire layer material, except the supporting material, must be accessible by diffusion to the liquid to be examined. "Diffusion" is quite generally understood as the migration of liquid into the layer material whether it be by capillary forces, centrifugal force etc. Radially positioned reagent layer units can, if desired, be arranged in such a way that they are not in contact with one another and a free space remains between them. This free space can be treated in such a way that it is water-resistant or water-repellent. Aqueous liquid applied to a central site treated in this manner is then absorbed by the adjoining reagent layer units.

Multilayered test carriers denoted analytical elements are known from EP-B 0 209 032 in which it is intended to prevent liquid from one test matrix reaching another test matrix on the same test carrier. For this the multilayered analytical element is composed of at least one layer containing reagent and an adjacent layer which can be melted by heating. When such a structure of layers is cut with ultrasound and/or laser energy the edges of the layers are welded together. In this way the edges are more or less sealed and it is thus intended to prevent liquid from flowing over from one test matrix into another on the same test carrier.

EP-A 0 185 982 describes in particular dipstick tests which are intended to be suitable for the simultaneous detection of several parameters. For this the various reagents necessary for detecting the respective parameters must be present in adjacent test zones on a test carrier. The overflow of liquid from one test zone into the adjoining one can lead to interferences. In order to prevent this overflowing it is proposed that open-celled, natural or synthetic materials be used as reagent carrier materials in which the cell openings can be closed at certain sites by heat or ultrasonic treatment so that separate reagent matrices are obtained which are effectively isolated from one another.

Whereas it was known from the aforementioned state of the art that boundaries which are intended to prevent a flow of liquid from one site to another can be generated in multilayer test devices by local heat treatment of test matrices i.e. carrier materials, EP-A 0 443 231 concerns multilayered so-called "test cards" with boundaries to the flow of liquids in order to direct the sample liquid from one site to another. Such liquid boundaries can inter alia be liquid flow barriers which have been generated by ultrasound or heat or barriers which have been formed by welding. The suction and pump action between two layers of different porosity is emphasized as an essential feature of the multilayered test cards. A first layer must be able to readily conduct liquid into a second layer necessary for cooperation. For this it is necessary that this second layer is capable of absorbing liquid well. The various functional zones within the individual layers are completely isolated from one another by liquid boundaries. Only by placing layers on top of one another in such a way as to generate overlapping areas which conduct liquid between the layers, liquid from a first layer can reach a second layer and from there return to the first layer at a zone which is different from the starting point. Thus the various functional zones are located in different layers or they are completely separated from one another within the same layer by means of liquid flow barriers. Thus apparently within the multilayered test card there are zones impregnated with reagent of various layers which are in direct contact with one another.

A common feature of all multilayered test carriers and analytical elements for determining an analyte is their complicated construction from a manufacturing and technical point of view since as a rule each layer has to be treated separately and cut to size before the layers can be finally assembled to form a test carrier.

Therefore the object according to the present invention is to provide test carriers which are as simple as possible to manufacture and work reliably with small sample volumes, and which are easy to handle and to interpret by the user.

This object is achieved by the present invention as characterized by the patent claims.

The invention concerns a test carrier for determining an analyte in a liquid sample containing a layer of a flat shaped material with at least one absorbent sample application area and at least one absorbent detection area with reagent necessary to determine the analyte and also, if desired, one or several further absorbent functional areas wherein in order to direct the sample liquid to be examined from the sample application area to the detection area optionally via one or several further absorbent functional areas boundaries are present within the flat shaped material through which sample liquid transport cannot take place. The test carrier according to the present invention is characterized in that all functional areas for the determination of an analyte are located within a single layer of the flat shaped material and that the individual functional areas are not in direct contact but instead are separated by absorbent connectors of the flat shaped material. According to the present invention the sample application area, detection area containing reagent and, if desired, further absorbent functional areas and absorbent connectors are defined by an all-round boundary in the flat shaped material which separates these areas and connectors altogether from the remainder of the flat shaped material in such a way that liquid transport can take place between the sample application area and detection area via one or more absorbent connectors and optionally via further absorbent functional areas but which prevents liquid transport from one of these areas or from the connector or connectors into the remaining flat shaped material outside the boundary.

The invention also concerns a process for the production of a test carrier according to the present invention which is characterized in that within a layer of absorbent material the material located around the absorbent areas and the connectors which link them is changed by heat treatment in such a way that it is no longer absorbent.

In so far the present invention also concerns the use of absorbent materials which can be deformed by heat for the production of a test carrier according to the present invention.

Finally the invention concerns a die or roller with elevations and depressions for the production of a test carrier according to the present invention. The die or roller is characterized in that the depressions correspond to the absorbent functional areas and the connectors which link them and the elevations correspond to the non-liquid-absorbing boundaries around the absorbent functional areas and around the connectors which link them.

The essential part of a test carrier according to the present invention is represented by a layer of the flat shaped material in which the functional areas and the connectors which link them are located. The following should at least be present as functional areas: a sample application area, that is a zone of absorbent material onto which the sample to be determined is to be applied and at least one detection area which contains either the complete reagent necessary for the determination of the analyte or a part thereof. If desired, the layer also contains one or several pre-reaction areas, that is zones which are either free of reagent or contain part of the reagent necessary for the determination which is not present in the detection area. The sample application area can also contain part of the reagent necessary for the determination of the analyte to be determined. In this respect a pre-reaction area which is free of reagent can serve to incubate a liquid which has been contacted and mixed with reagent in the sample application area.

The functional areas within the carrier material layer should not be in direct contact but rather should be separated by absorbent connectors of the flat shaped material.

Absorbent functional areas and the absorbent connectors which link them are isolated within the flat shaped carrier material from the surrounding layer material by a boundary according to the present invention to the extent that no sample liquid transport can take place through the boundary. Thus sample liquid can only move within the bounded area that is in the functional areas and the connectors which are located between them.

In principle all absorbent materials, in particular fibrous or porous materials which can absorb the sample liquid to be examined and in which this liquid can move in an analogous manner to that which is known from chromatography, come into consideration as the flat shaped carrier material for the test carriers according to the present invention. In fibrous materials the individual fibres can be present in a disordered state such as for example in fleeces or the fibres can be present in an ordered state which is for example the case in fabrics. Porous films or porous membranes can be used as the porous materials. Those absorbent materials are particularly preferred according to the present invention in which the liquid flow barrier around the functional areas and around the connectors which link them can be generated by heat without the aid of a further material. This can for example be accomplished when the entire absorbent material is itself deformable by heat or when the absorbent material contains constituents which are deformable by heat which is sufficient to form a boundary in the absorbent material that is not permeable to liquid. In this regard absorbent layers which are either entirely or partially constructed of thermoplastic plastics such as polyamide, polyester, cellulose ester, polypropylene or similar ones are particularly preferred. A fleece comprising 30 parts polyester, 20 parts viscose staple fibre, 30 parts copolyester and 20 parts polyvinyl-alcohol has proven to be especially suitable for use in a test carrier according to the present invention.

The carrier materials described above can be changed by local heat treatment in such a way that they are no longer absorbent and almost impermeable to liquids at these sites. Laser energy, ultrasound or any other type of means of generating heat or hot agents are suitable for such a heat treatment. Embossing tools such as dies or rollers which are either themselves warm or can be operated with the aid of agents or energies which generate heat such as for example ultrasound have proven to be particularly suitable according to the present invention. Such dies or rollers have elevations and depressions whereby the elevations generate the liquid-impermeable boundaries around the functional areas and around the connectors which link them when the die or the roller is pressed with its embossing side onto the absorbent layer. When the die or the roller is pressed onto the absorbent layer, the layer material is melted or at least sintered at the warm sites of the die elevations so that liquid transport is no longer possible within these sites. The depressions on the embossing site of the die correspond to the functional areas and to the connectors which link them. The depressions must therefore be deep enough so that when the embossing side of the die is pressed onto the absorbent material the absorbency is not impaired to a substantial extent. Suitable die and roller materials are metals and alloys known from tool manufacturing which have an adequate heat conductivity. The surface of the die or roller which is used for the embossing should preferably be antiadhesive. This can for example be accomplished by coating with Teflon TM (Teflon is a trademark of DuPont).

It is also possible according to the present invention to generate the liquid-impermeable boundary around the functional areas and around the connectors which link them by using a material which is different from the absorbent layer. For example it is possible to underlay an absorbent layer made of material which is not deformed by heat with a material which is heat deformable. By local heat treatment of the heat deformable material through the absorbent layer which is not deformed heat it is possible that the heat deformable material, optionally also under pressure, penetrates into the absorbent layer and makes this impermeable to liquid at these sites. Thus, it is for example possible to underlay an absorbent layer made of material which is not deformable by heat with a layer of heat deformable material and to press a hot embossing tool or an embossing tool operated by agents which generate heat onto the absorbent layer in such a way that the heat deformable material located under the elevations of the die or the roller is changed in such a way that it penetrates into the absorbent layer and makes it impermeable to liquids at these sites.

The latter method can also be used in particular when the rigidity of the absorbent layer material by itself is low and it is intended to combine this material with a supporting layer to stabilize it and improve the handling.

In this way it is for example possible to combine cellulose fleece, fabrics made of monofilament or multifilament yarns of high melting point, glass fibre fabrics or glass fibre fleeces with a foil coated with hot-setting adhesive which is itself heat resistant. Hot-setting adhesives which are particularly suitable are the Elvax TM adhesives from the DuPont Company or the Dynapol TM adhesives from the Dynamit Nobel company. Polyester foils can be readily used as temperature-resistant carrier foils which have a stable form.

The liquid flow barrier within the absorbent layer which directs the liquid can be thin and merely represent something like a border around the functional areas and the connectors which link them. It can, however, also be constructed in such a way that within the entire layer only the functional areas and the linking connectors possess the absorbent property of the material. In any case it is of primary importance that liquid cannot go outside the functional areas and the connectors which link them.

The functional areas can have many different forms. They can be round, oval, rectangular, square or have other forms provided this appears appropriate for the function of the zone. Round functional areas have proven to be particularly suitable. The size of the functional areas can also be adapted over a wide range to suit the requirements. It has to be taken into account that large surface dimensions of the functional areas require larger sample or liquid volumes than smaller area dimensions. Areas of 10 mm$^2$ to 50 mm$^2$ for the functional zones have proven to be preferable for the test carriers according to the present invention.

With regard to surface area, the absorbent connectors which link the functional areas are thin zones of the absorbent layer material compared to the width or the diameter of the functional areas which they connect. As a rule the connectors are free of reagent. They preferably have a width of 0.5 mm to 3.0 mm and a length of 2 mm to 10 mm.

The thickness of the absorbent layer within the functional areas and the connectors which link them corresponds approximately to the thickness of the absorbent layer material used originally for the manufacture of the test carrier according to the present invention and is about 0.1 mm to 1.0 mm. Also in this case it is possible to have deviations towards higher or lower values depending on whether one is able to or intends to work with more or less liquid. In addition the choice of thickness of the absorbent layer material and form and dimensions of the functional areas and connectors which link them enables the time course of the method of determination on the test carrier to be controlled without external manipulations. Thus a defined volume of liquid requires more time to fill a large functional area than would be necessary for a smaller functional area. Long connectors result in a longer delay between the time when the liquid leaves one functional area and reaches another functional area.

In general it has proven to be advantageous when the surface area of the sample application area is larger than that of the detection area. In the case that a pre-reaction area is located between the sample application area and detection area this should preferably have a surface area which is between the size of the sample application area and that of the detection area. When carrying out the method of determination it has in general proven to be advantageous when the liquid reaches a functional area of smaller surface area from one of larger surface area within the absorbent layer.

The connectors linking the functional areas can be straight, bent, angled or be present in other possible designs. It has proven to be particularly advantageous for the test carrier according to the present invention when the connectors between the linked functional areas are straight, that is represent the shortest distance between two functional areas arranged at a particular distance from one another.

In order to produce a test carrier according to the present invention the material in the absorbent layer located around the functional areas and around the linking connectors has to be changed in such a way by heat treatment that it is no longer absorbent. As already described above this is preferably achieved with an embossing tool such as a die or a roller which has depressions in the embossing area which correspond to the functional areas and the connectors which link them and conversely has elevations which produce the liquid-impermeable boundaries around the functional areas and the connectors which link them. It has proven to be advantageous for the embossing process when the absorbent material, which is optionally underlayed with meltable material that does not correspond to the absorbent material, lies on a flat surface in such a way that the warm embossing tool or the embossing tool operated by agents which generate heat presses the absorbent material against the flat surface. In this process, heat and pressure should be of sufficient magnitude that the absorbent material looses its absorbent property throughout the entire depth at the positions of the elevations on the embossing tool. Instead of a flat counter-pressure surface it is, however, also possible to use a second embossing surface as a counter-pressure surface which produces a mirror image pattern of the embossing tool. In the latter case the absorbent material is for example processed between two embossing dies which in relation to one another are designed in such a way that when pressed together they generate an exactly matching pattern of functional areas and connectors which link them on the under side as well as on the upper side of the absorbent material. If an embossing roller is used the counter-pressure surface does not have to be flat but can also be curved. In any case the roller must be able to produce the desired pattern with thee embossing elevations on the absorbent layer over the entire roller width.

As a rule the reagent necessary for the analyte determination is applied after the embossing process to the site or sites on the absorbent material which have been provided therefor. Although this can also take place before the embossing process, the sequence of first embossing and then applying reagent has, however, proven to be advantageous. The reagent necessary for the analyte determination can be applied to the functional areas provided for this purpose by various methods. Printing methods such as for example screen printing, tampon printing, ink jet, flexo printing and dosing methods such as needle dosing, partial roller application, roll-reverse roller application have proven to be advantageous. Such methods are known from the state of the art and do not need to be described in more detail here. In particular the ink jet method has proven to be an advantageous method.

The reagent for the analyte determination is either applied completely to the detection area or the reagent constituents are divided between one or several pre-reaction areas and the detection area in such a way that the first step or steps of a multistep detection reaction take place in one or several pre-reaction areas and the last reaction step which generates the test signal takes place in the detection area. In certain circumstances it may, however, also be appropriate not to allow any chemical reaction to proceed in the detection area itself but rather to use this zone to concentrate the substance which generates the test signal. It has proven to be particularly advantageous for the test carrier according to the present invention when the detection is carried out colorimetrically. In this process a colour is formed or a change in colour occurs. This effect can be evaluated visually or measured quantitatively by photometry.

In addition to applying the reagent necessary for the determination of an analyte it may also prove to be appropriate to apply further substances to the functional areas. For example it may be expedient for the determination of an analyte in whole blood to treat the sample application area with substances which result in a separation of erythrocytes from the whole blood so that only plasma or serum reach the functional areas which are located after the sample application area. Substances which agglutinate erythrocytes have proven to be particularly advantageous for this such as those which are known from EP-B 0 133 895.

If the layer which supports the functional areas and the connectors which link them has an adequate rigidity after generating the boundary to direct the liquid transport then this material can be used without a further supporting layer as a test carrier for the determination of an analyte. However, it will generally prove to be advantageous to mount the layer which is provided with the liquid flow barrier that directs the sample liquid and which supports the functional areas and the connectors linking them as well as the reagents necessary for the determination reaction on a rigid supporting layer to facilitate handling. Translucent or opaque rigid materials such as plastic foils, glass, metal etc. can be used as the supporting layer. Rigid plastic foils made of polystyrene or polyester have proven to be particularly advantageous. The layer carrying the functional areas can be mounted on the supporting layer by methods such as those which are known to an expert from the state of the art for the manufacture of multilayered test carriers. A simple method is for example mounting by means of double-sided adhesive tape or by means of hot-setting adhesive.

A particularly simple method for increasing the rigidity of the absorbent layer has already been described above in connection with the description of the production of the boundary in the absorbent material which directs liquid flow. In this case the absorbent layer is laminated by heat together with a heat deformable layer at positions which are intended not to be permeable to liquid in such a way that molten material from the heat deformable layer generates the liquid-impermeable boundary in the absorbent layer. This lamination, in particular this flat connection which merely omits the absorbent zones of the functional areas and the connectors which link them enables the production of a rigid test carrier in a simple process.

In order to carry out the determination of an analyte in a sample liquid—according to the present invention body fluids such as blood, plasma, serum or urine are used in particular but all other types of liquids can be used—sample liquid is applied to the sample application zone or the test carrier with the sample application zone is dipped into the sample liquid to be examined.

Either during sample application or immersion in the sample liquid enough liquid is taken up so that it is sufficient to moisten the entire absorbent material of the functional areas and the connectors which link them or, in case the amount of sample liquid is not adequate sufficient liquid without the analyte to be determined is added after sample application so that the liquid suffices to fill all absorbent areas with liquid. When blood, plasma or serum is examined the sample is usually applied to the sample application zone. When examining urine the test carrier is usually dipped into the liquid to be examined.

After the sample to be examined has been applied to the sample application zone or after dipping the test carrier into the liquid to be examined, the liquid spreads out radially in the sample application zone until it meets the thermally generated boundaries. In places where the liquid does not meet liquid flow barriers the liquid migrates into dry absorbent material. In this way the liquid front finally reaches the detection zone via one or several pre-reaction zones which may be present and via the connectors which link the functional areas. Once the absorbent layer in the region of the detection zone has been completely absorbed with liquid there is no further possibility for the liquid to spread out and the liquid transport comes to a standstill. Under certain circumstances it may, however, also be appropriate to locate a further empty functional area after the detection zone which is linked to this via an absorbent connector so that liquid can be absorbed through the detection area. Such a design can for example prove to be necessary when a larger amount of liquid is required to bring all the substance to be detected into the detection area than would be the case when liquid transport already came to a standstill when the detection area had been filled. Such a zone located after the test zone could, in accordance with its function, be for example designated suction zone. It is of course also possible to position several suction zones after the detection zone. This could for example be arranged in such a way that the detection area is linked to a first suction zone via an absorbent connector and this first suction zone is in turn linked to a second suction zone via a further absorbent connector. However, the detection zone could also be linked directly to two suction zones via two absorbent connectors.

Just as there are many possibilities for the geometric arrangement of the functional areas for the determination of an analyte in a sample liquid, it is also possible to determine several analytes simultaneously on one test carrier according to the present invention. For this purpose several sample application zones can be present on a single test carrier each of which is itself connected by means of absorbent connectors to detection areas, optionally via pre-reaction areas, without the respective functional areas for the determination of one analyte being connected to the functional areas for the determination of another analyte. In such a case several independent sample application areas would be present next to one another on a single test carrier with the previously described options for positioning the other functional areas.

However, it is also possible that on a test carrier according to the present invention for the determination of several analytes in a sample liquid a common sample application area is linked via absorbent connectors to the other respective functional areas which are necessary for the simultaneous determination of several analytes. Thus starting from a common sample application zone there is a branching to the functional areas necessary for the determination of several different analytes which in turn are not connected together. The only common site is the sample application area. Under certain circumstances it is also possible that not only the sample application area but also one or several pre-reaction areas are used jointly by the sample liquid which is to be examined for several analytes before it branches into the functional areas for the determination of the individual analytes. For example, it could also be possible to apply whole blood to a common sample application area which is transported to a pre-reaction area via an absorbent connector provided with substances which agglutinate erythrocytes so that starting from this pre-reaction area plasma or serum can be transported for further reaction. Starting from this pre-reaction area plasma or serum could be branched into functional areas for the determination of the individual analytes whereby the subsequent functional areas for the determination of the individual analytes are no longer connected to one another.

A test carrier for the determination of several analytes in a sample liquid can also be constructed in such a way that several test carriers according to the present invention of the aforementioned type for the determination of a single analyte are layered on top of one another in such a way that they are connected to one another via the respective sample application zones but otherwise are separated from one another in such a way that liquid cannot be transported from one absorbent layer into another.

BRIEF DESCRIPTION OF THE DRAWINGS

It is intended to elucidate embodiments of the test carrier according to the present invention in more detail on the basis of the figures.

FIG. 1a and b show how starting with an absorbent fleece which is pressed between the warm elevations (3) and (4) of two embossing plates of two dies the boundary (2) which is not permeable to liquid is formed and the functional area (1) remains unchanged as an absorbent area.

FIG. 4 shows a top view of a square test carrier according to the present invention in which the sample application area (9) and detection area (11) are connected together via an absorbent connector (10). The functional areas (9) and (11) and the absorbent connector (10) are all surrounded by material (12) which has been made non-absorbent by heat treatment and into which no liquid can enter from the absorbent areas. The detection area (11) is smaller than the sample application area (9). The absorbent connector (10) is thin compared to the diameters of the functional areas (9) and (11).

Figure 1A:
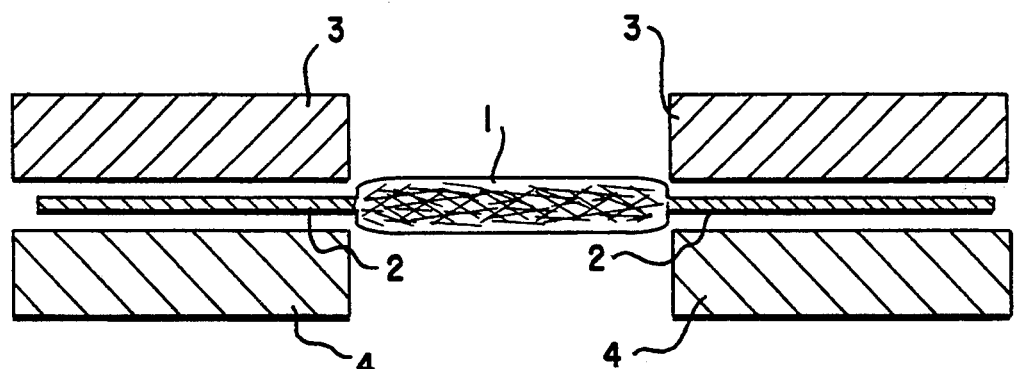
FIG. 1a and 1b as well as FIG. 2a and FIG. 3a show a cross-section through a functional area on an analytical device according to the present invention together with a cross-section through an embossing device which is used to generate this functional area.
Figure 1B:
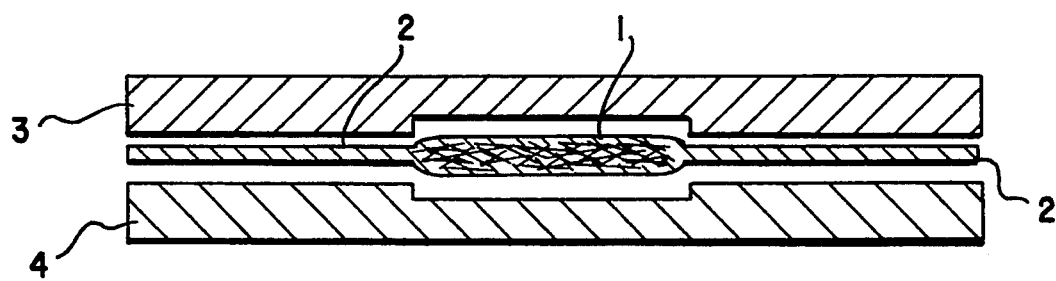
Figure 2A:
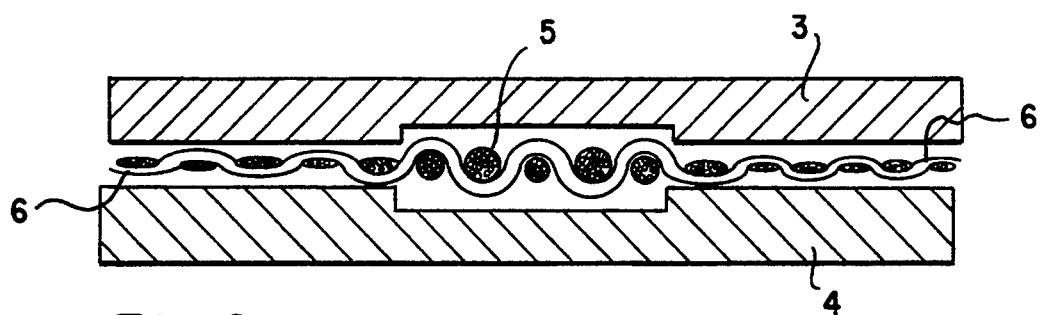
In FIG. 2a and b, a fabric is shown as an absorbent layer from which the liquid flow barrier (6) which is impermeable to liquid is formed around the functional area (5) by heat treatment under pressure using the embossing plates (3) and (4) of two dies. Fibres which are aligned regulary and woven together are recognizable within the functional area (5).
Figure 2B:
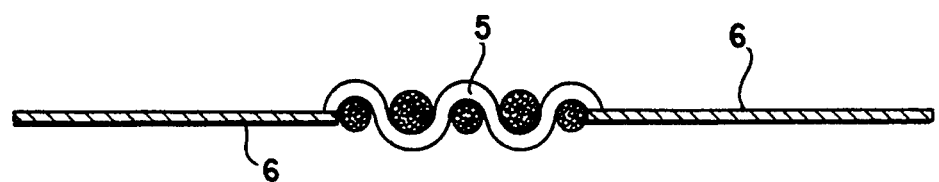
FIG. 2b and 3b each show a cross-section through a functional area on a test carrier according to the present invention.
Figure 3A:
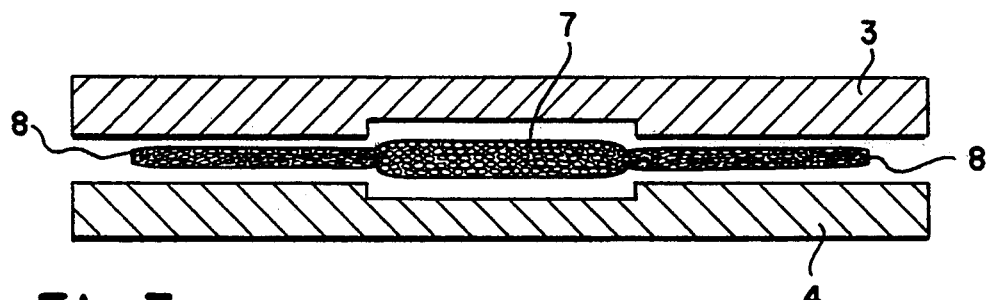
FIG. 3a and b show a cross-section through a test carrier according to the present invention in which the absorbent layer consists of a porous membrane whose structure remains unchanged in the region of the functional zone (7) whereas the boundary (8) has been pressed together under the influence of heat using the embossing plates (3) and (4) of two dies in such a way that this zone is no longer permeable to liquid.
Figure 3B:
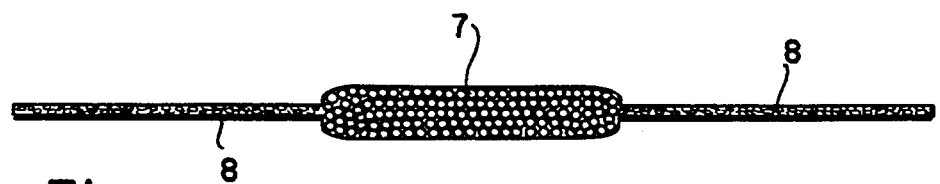
Figure 4:
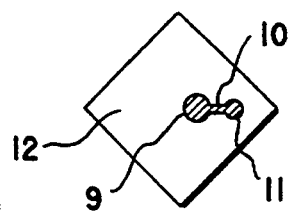
FIG. 4, 5a and 6 show a top view of different embodiments of the test carrier according to the present invention for the determination of an analyte.
Figure 5A:
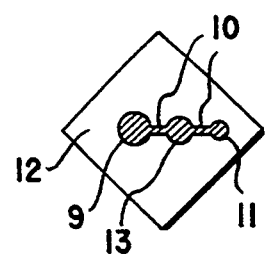

An analytical device according to the present invention is shown in FIG. 5a which differs from that shown in FIG. 4 in that a pre-reaction area (13) is located between the sample application area (9) and the detection area (11) and is linked via absorbent connectors (10) to the sample application area (9) as well as to the detection area (11). With regard to surface area the size of the pre-reaction area (13) is between that of the sample application area (9) and that of the detection area (11).

Figure 5B:
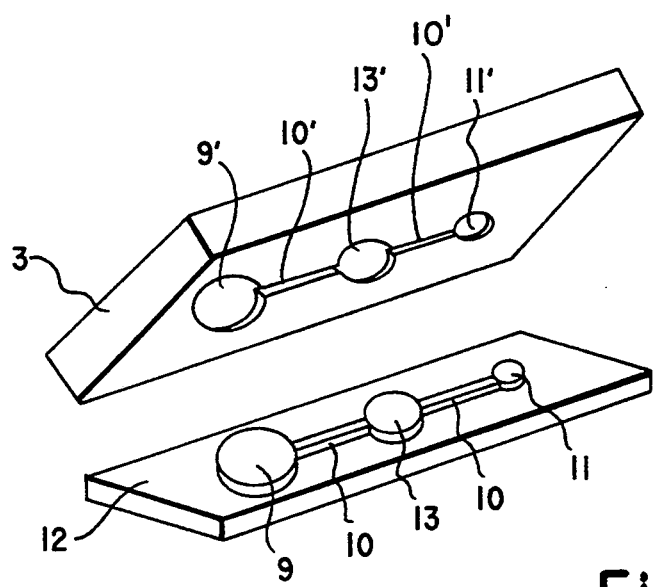
FIG. 5b shows a slanted perspective view of a test carrier for the determination of an analyte according to the present invention together with the respective embossing device.

FIG. 5b shows an oblong variant of the test carrier according to FIG. 5a with functional areas (9, 13, 11) and connectors (10) linking these together and a corresponding embossing plate (3). The depressions (9', 11' and 13' as well as 10') of the embossing plate correspond to the absorbent functional areas (9, 11 and 13) and to connectors (10) of the test carrier.

Figure 6:
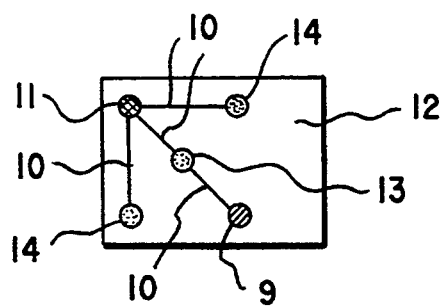

FIG. 6 shows a top view of an analytical device according to the present invention which differs from the test carrier shown in FIG. 5a in that the detection area (11) is connected via absorbent connectors (10) to two suction zones (14). Sample, which is applied to the sample application area (9), is transported via connector (10) into the pre-reaction area (13) and from there into the detection area (11) via the absorbent connector (10). If there is an adequate amount of liquid the liquid spreads out from the detection area (11) over the connectors (10) into the suction zones (14).

Figure 7:
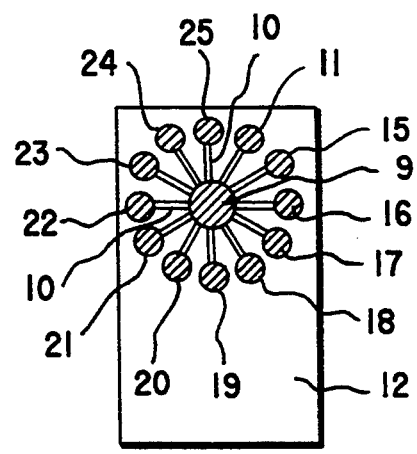
FIG. 7-9 show a top view of embodiments of the analytical device according to the present invention for the determination of several analytes in one layer.

FIG. 7 shows a top view of a test carrier according to the present invention for the determination of several analytes in one layer. Detection areas for different analytes (11, 15, 16, 17, 18, 19, 20, 21, 22, 23, 24, 25) are positioned around a sample application area (9) via absorbent connectors (10). In this way it is possible to simultaneously determine several parameters from one sample.

Figure 8:
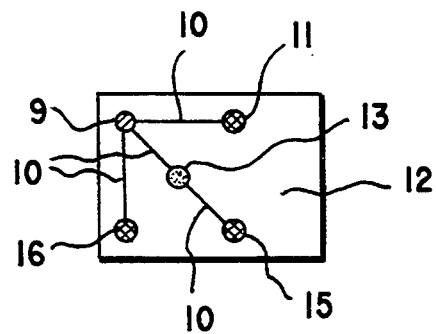

FIG. 8 shows another possibility for a geometric design of functional areas in an analytical device according to the present invention for the determination of several analytes in one layer. The sample application area (9) is connected via absorbent connectors (10) to the detection areas (11) and (16) for two analytes. The determination of a third analyte requires a pre-reaction. Therefore the sample application area (9) is connected via an absorbent connector to the pre-reaction area (13) which in turn is connected via an absorbent connector (10) to the detection area for the third analyte (15). In this way three parameters can be determined simultaneously from one sample. Such a design could for example be suitable for the determination of triglyceride, cholesterol and HDL cholesterol in blood, plasma or serum.

Figure 9:
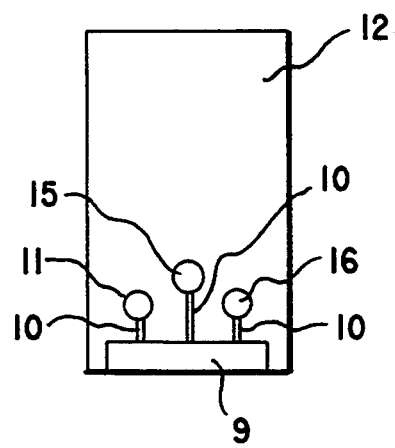

FIG. 9 shows a dipstick test for the determination of several analytes in a sample. When the test strip is dipped into the sample liquid to be examined so that the sample application area is wetted, liquid rises up via the sample application area (9) and the connectors (10) into the detection areas (11, 15, 16).

Figure 10:
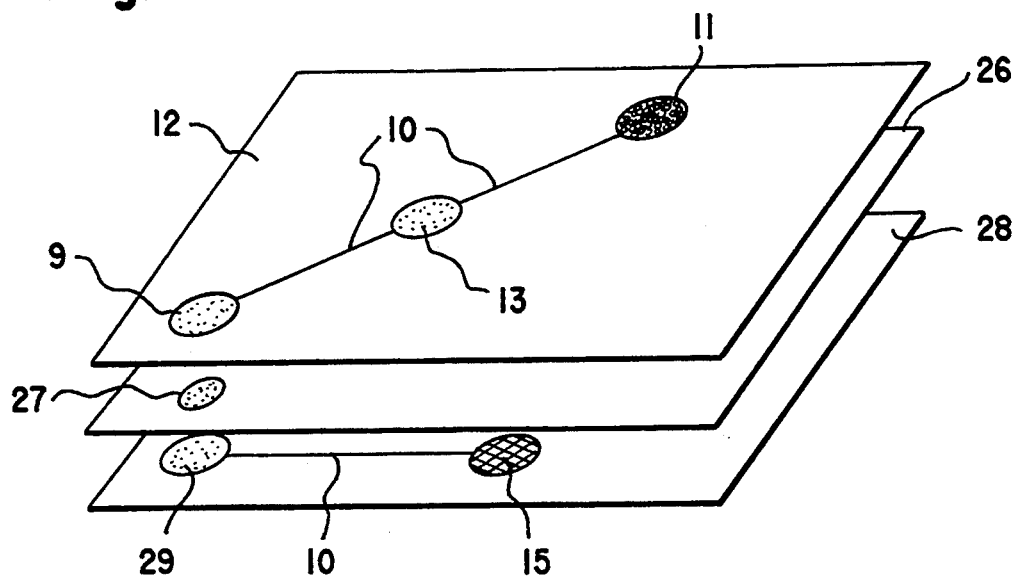
FIG. 10 shows a slanted perspective view of the construction of a test carrier according to the present invention for the determination of two analytes in two layers.

FIG. 10 shows a test carrier according to the present invention for the determination of two analytes in two layers. Liquid sample can be applied to the sample application area (9) in layer (12), which is only absorbent in the region of the functional areas (9, 13, 11) and the connectors (10) but otherwise cannot transport liquid, and from where sample liquid is transported via the connectors (10) through the pre-reaction area (13) into the detection area (11) where the first analyte is determined. From the sample application area (9) liquid penetrates simultaneously through the barrier layer (26) which apart from zone (27) is not permeable to liquid and reaches the sample application area (29) in layer (28) which is only absorbent in the region of the functional areas (29, 15) and the connector (10) but otherwise cannot transport liquid. From there the liquid to be examined is transported via the absorbent connector (10) into the detection area (15). Here the second analyte is detected. If the layers (12, 26 and 28) are transparent, colorimetric test reactions can be determined simultaneously in the detection areas (11) and (15) from one side of the test carrier. If layer (26) is not transparent the detection reaction of one of the analytes can be observed from one side of the test carrier and the detection reaction of the other analyte can be observed from the opposite side of the test carrier.

As can be gathered from the description above a feature of the test carrier according to the present invention is a basically very simple construction. Its manufacture is also correspondingly simple. At the same time this construction offers a multitude of alternatives for the detection of various analytes whereby the different geometric designs of the functional areas only require different embossing dies or rollers. It is above all particularly advantageous that a test carrier according to the present invention cannot only be manufactured in partial steps but perfectly well in a production line in continuous operation.

A production plant for analytical devices according to the present invention which is composed of the following equipment has proven to be particularly suitable:

—embossing equipment with embossing dies or embossing rollers
—reagent application station for the application of the necessary reagents on the functional areas by means of ink jet
—drying channel preferably an IR or microwave drier
—separation plant which cuts the individual test carriers from the processed strip of material.

This can be directly linked to a packaging unit.

Since the exterior shape of the test carriers according to the present invention can be designed in a way which is largely independent of the function of the detection reaction, geometries are possible which are amenable to automatic feeding and operations in automatic analysers.

The sample volume and consequently also the required amounts of reagent can be kept very small. Thus, depending on the absorbent material and chosen geometry, sample volumes between 3 and 30 µl are usually sufficient.

It is intended to further elucidate the invention by the following examples, but these examples are not intended to limit the invention to the concrete embodiments.

EXAMPLE 1

Glucose determination a) Production of a test carrier according to FIG. 4

An absorbent fibre fleece was used consisting of
- 30 parts polyester fibres
- 20 parts viscose staple fibres
- 30 parts copolyester fibres (hot-setting adhesive fibres, Grilene K 170 from Ems-Grilon SA, Domat/Ems, Switzerland)
- 20 parts polyvinyl alcohol fibres with a weight per area of 140 g/m$^2$ and a thickness of 0.5 mm.

The fleece was manufactured on an inclined screening machine used as a paper machine (Voith Co., Heidenheim, Germany). For this the fibres suspended in water were pumped onto an inclined screen. While the liquid flowed away or was sucked off by vacuum the fibres orientated on the screen surface and were dried as a fleece over a drying cylinder. The drying was carried out at 125° C. until a final humidity of 0.5-1.5% by weight was achieved.

The embossing dies used for the embossing had a dimension of 40×40×20 mm and were made of brass.

The embossing shape was engraved into the dies; the shape was two circular recesses joined by a connector. One of the circular recesses had a diameter of 6 mm, the other circular recess had a diameter of 4 mm. The recess for the linking connector had a width of 2 mm and a length of 4 mm. The depth of the recesses in the embossing die was 4 mm.

The embossing die was preheated to 210° C. for embossing the absorbent material; the embossing itself was carried out at an applied pressure of 0.2 Mpas over a pressing time of 2 seconds.

b) Impregnation

In order to impregnate the detection area (11) with the reagent necessary for the determination of glucose, 10 µl of an acetone solution containing
- 1% by weight 3,3',5,5 tetramethylbenzidine (TMB) and
- 1.2% by weight dioctyl sodium sulfosuccinate (DONS)

was pipetted onto this site and dried for 10 minutes at 60° C.

Afterwards 10 µl of a solution of
- glucose oxidase (250 kU/l) and
- peroxidase (500 kU/l)

in phosphate buffer solution (pH 7.0; 0.1 mol/l) was also applied to the detection area (11) and dried for 30 minutes at 60° C.

c) Procedure for the glucose determination

After application of ca. 30 µl control sera containing glucose onto the sample application area (9) a concentration-dependent homogeneous blue colour of different intensities is formed in the detection area (11) within 10 seconds.

EXAMPLE 2:

Determination of cholesterol

For the impregnation with the reagent necessary for the determination of cholesterol, 10 µl of an acetone solution containing
- 1% by weight TMB and
- 1.2% by weight DONS was pipetted onto the detection area (11) of a test carrier according to FIG. 4 which was manufactured as in example 1a) and dried for 10 minutes at 60° C.

10 µl of the following enzyme solution was pipetted onto this dried detection area (11) provided with indicator:
- cholesterol esterase (500 kU/l)
- cholesterol oxidase (50 kU/l)
- peroxidase (500 kU/l)
- MgCl$_2$. 6H$_2$O (25 mmol/l)

in phosphate buffer (pH 7.0; 0.1 mol/l)

Subsequently it is dried for 30 minutes at 60° C.

When a concentration series of control sera containing cholesterol are applied to the sample application area a concentration-dependent homogeneous blue reaction colour of different intensities is formed in the detection area (11) after ca. 10 seconds.

The following documents are hereby incorporated by reference:
U.S. Pat. No. 4,235,601
German Patent No. DE-A-3 222 366
European Patent No. EP-A-0 166 365
European Patent No. EP-B-0 209 032
German Patent No. DE-A-2 934 760
European Patent No. EP-A-0 185 982
European Patent No. EP-A-0 443 231
European Patent No. EP-B-0 133 895.

We claim:

1. An analytical device for determining an analyte in a liquid sample, said analytical device comprising:

a layer of flat material having at least one absorbent sample application area and at least one absorbent detection area, said at least one absorbent detection area having a reagent for determining the analyte, said absorbent sample application area and said absorbent detection area being disposed within a liquid impermeable boundary, said sample application area not containing all reagents necessary for analyte detection and determination, wherein said layer of flat material further comprising at least one absorbent connector, said absorbent connector being disposed such that said sample application area and said detection area are connected by said absorbent connector, wherein said liquid impermeable boundary and said absorbent connector prevent liquid from being transported between said at least one sample application area and said at least one detection area, except through said absorbent connector.

2. An analytical device as recited in claim 1, wherein said at least one absorbent detection area is a plurality of detection areas, each of said plurality of detection areas being connected to said sample application area by a corresponding plurality of said absorbent connectors.

3. An analytical device as recited in claim 2, wherein said at least one sample application area is a plurality of sample application areas.

4. An analytical device as recited in claim 1, wherein said layer of flat material is heat-meltable material wherein said liquid-impermeable boundaries comprise heat treated areas of said heat-meltable material, wherein the heat treatment reduces the absorbency of the heat treated areas.

5. An analytical device as recited in claim 1, wherein said liquid-impermeable boundary comprises a material which is not a same material as the layer of material comprising the absorbent sample application area and the absorbent detection area.

6. An analytical device as recited in claim 1, wherein a surface area of said at least one sample application area is larger than a surface area of said at least one detection area.

7. An analytical device as recited in claim 1, wherein the at least one sample application area and the at least one detection area comprise a fibrous material.

8. An analytical device as recited in claim 1, wherein said at least one sample application area, detection area, and absorbent connector comprise a porous material.

9. A process for manufacturing an analytical device for determining an analyte in a liquid sample, said process comprising the steps of:
 providing a layer of flat absorbent first material;
 forming at least one absorbent sample application area on said layer of flat first material, said sample application area not containing all reagents necessary for analyte detection and determination;
 forming at least one absorbent detection area on said layer of flat first material;
 forming at least one absorbent connector connecting said at least one sample application area and said at least one detection area,
 wherein said at least one sample application area, said at least one detection area, and said absorbent connector are disposed within a liquid impermeable boundary, said liquid impermeable boundary being formed during said forming steps, and wherein said at least one absorbent detection area includes a reagent for determining the analyte in a liquid sample.

10. A process for manufacturing an analytical device as recited in claim 9, wherein said steps of forming said sample application area, forming said detection area, and forming said absorbent connector comprises heat treatment of portions of said layer of flat first material forming the liquid impermeable boundaries.

11. A process for manufacturing an analytical device as recited in claim 10, wherein said heat treatment is performed with ultrasound.

12. A process for manufacturing an analytical device for determining an analyte in a liquid sample, said process comprising the steps of:
 providing a layer of flat absorbent first material;
 forming at least one absorbent sample application area on said layer of flat first material forming at least one absorbent detection area on said layer of flat first material, wherein said first absorbent first material is heat-deformable;
 forming at least one absorbent connector connecting said at least one sample application area and said at least one detection area,
 wherein said at least one sample application area, said at least one detection area, and said absorbent connector are disposed within a liquid impermeable boundary, said liquid impermeable boundary being formed during said forming steps, and wherein said at least one absorbent detection area includes a reagent for determining the analyte in a liquid sample.

13. A process for manufacturing an analytical device as recited in claim 9, further comprising the steps of:
 providing a heat-deformable second material;
 locating said heat-deformable second material under said layer of flat first material, wherein said steps of forming the sample application area, forming the detection area, and forming the absorbent connector are performed by heat-treatment of the heat-deformable second material such that the absorbent flat first material is affected in selected areas so that it is no longer absorbent.

14. A process for manufacturing an analytical device for determining an analyte in a liquid sample, said process comprising the steps of:
 providing a layer of flat absorbent first material;
 forming at least one absorbent sample application area on said layer of flat first material forming at least one absorbent detection area on said layer of flat first material;
 forming at least one absorbent connector connecting said at least one sample application area and said at least one detection area,
 providing a die having a plurality of elevations and depressions formed therein, wherein said steps of forming the sample application area, forming the detection area, and forming the absorbent connector is performed by contacting the layer of flat first material with said die;
 wherein said at least one sample application area, said at least one detection area, and said absorbent connector are disposed within a liquid impermeable boundary, said liquid impermeable boundary being formed during said forming steps, and wherein said at least one absorbent detection area includes a reagent for determining the analyte in a liquid sample.

15. A process for manufacturing an analytical device as recited in claim 14, wherein an outer surface of said die is coated with a non-stick material.

16. A process for manufacturing an analytical device as recited in claim 15, wherein said non-stick material comprises Teflon TM.

17. An analytical device as recited in claim 1, wherein said layer of flat material has a consistent chemical make-up throughout.

18. An analytical device for determining an analyte in a liquid sample, said analytical device comprising:
 a layer of flat material having at least one absorbent sample application area and at least one absorbent detection area, said at least one absorbent detection area having a reagent for determining the analyte, said absorbent sample application area and said absorbent detection area being disposed within a liquid impermeable boundary, wherein
 said layer of flat material further comprising at least one absorbent connector, said absorbent connector being disposed such that said sample application area and said detection area are connected by said absorbent connector,
 wherein said liquid impermeable boundary and said absorbent connector prevent liquid from being transported between said at least one sample application area and said at least one detection area, except through said absorbent connector, and wherein said sample application area, said absorbent connector, said detection area, and said liquid impermeable boundary of said layer of flat material comprise the same chemical elements.

19. An analytical device as recited in claim 1, wherein said sample application area and said detection area are located on a same surface of said layer of flat material.

20. An analytical device as recited in claim 1, wherein said layer of flat material comprises a combination of heat-meltable and non-heat-meltable material, wherein said liquid impermeable boundaries comprise heat treated areas of said combination of heat-meltable and non-heat meltable material, wherein heat treatment reduces absorbance of the heat-treated areas.

21. An analytical device for determining an analyte in a liquid sample, said analytical device comprising:
a layer of flat material having at least one absorbent sample application area and at least one absorbent detection area, said at least one absorbent detection area having a reagent for determining the analyte, said absorbent sample application area and said absorbent detection area being disposed within a liquid impermeable boundary, wherein
said layer of flat material further comprising at least one absorbent connector, said absorbent connector being disposed such that said sample application area and said detection area are connected by said absorbent connector, said at least one absorbent connector having a cross-section which is less than a cross-section of the sample application area and a cross-section of the detection area,
wherein said liquid impermeable boundary and said absorbent connector prevent liquid from being transported between said at least one sample application area and said at least one detection area, except through said absorbent connector.

22. An analytical device as recited in claim 21, wherein said at least one detection area is a plurality of detection areas, each of said plurality of detection areas being connected to said sample application area by a corresponding plurality of said absorbent connectors.

23. An analytical device as recited in claim 22, wherein said at least one sample application area is a plurality of sample application areas.

24. An analytical device as recited in claim 21, wherein said layer of flat material is heat-meltable material wherein said liquid-impermeable boundaries comprise heat treated areas of said heat-meltable material, wherein the heat treatment reduces the absorbency of the heat treated areas.

25. An analytical device as recited in claim 21, wherein said layer of flat material comprises a combination of heat-meltable and non-heat-meltable material, wherein said liquid impermeable boundaries comprise heat treated areas of said combination of heat-meltable and non-heat-meltable material, wherein heat treatment reduces absorbance of the heat-treated areas.

26. An analytical device as recited in claim 21, wherein said liquid-impermeable boundary comprises a material which is not a same material as the layer of material comprising the absorbent sample application area and the absorbent detection area.

27. An analytical device as recited in claim 21, wherein a surface area of said at least one sample application area is larger than a surface area of said at least one detection area.

28. An analytical device as recited in claim 21, wherein the at least one sample application area and the at least one detection area comprise a fibrous material.

29. An analytical device as recited in claim 21, wherein at least one sample application area, detection area, and absorbent connector comprise a porous material.

30. An analytical device as recited in claim 21, wherein said layer of flat material has a consistent chemical make-up throughout.

31. An analytical device as recited in claim 21, wherein said sample application area and said detection area are located on a same surface of said layer of flat material.

32. An analytical device for determining an analyte in a liquid sample, said analytical device comprising:
a layer of flat material having at least one absorbent sample application area and at least one absorbent detection area, said at least one absorbent detection area having a reagent for determining the analyte, said absorbent sample application area and said absorbent detection area being disposed within a liquid impermeable boundary, said layer of flat material being heat-meltable material, wherein the liquid-impermeable boundaries comprise heat treated areas of said heat-meltable material, wherein the heat treatment reduces the absorbency of the heat treated areas, wherein
said layer of flat material further comprising at least one absorbent connector, said absorbent connector being disposed such that said sample application area and said detection area are connected by said absorbent connector,
wherein said liquid impermeable boundary and said absorbent connector prevent liquid from being transported between said at least one sample application area and said at least one detection area, except through said absorbent connector.

33. An analytical device as recited in claim 32, wherein said at least one detection area is a plurality of detection areas, each of said plurality of detection areas being connected to said sample application area by a corresponding plurality of said absorbent connectors.

34. An analytical device as recited in claim 33, wherein said at least one sample application area is a plurality of sample application areas.

35. An analytical device as recited in claim 32, wherein said liquid-impermeable boundary comprises a material which is not a same material as the layer of material comprising the absorbent sample application area and the absorbent detection area.

36. An analytical device as recited in claim 32, wherein a surface area of said at least one sample application area is larger than a surface area of said at least one detection area.

37. An analytical device as recited in claim 32, wherein the at least one sample application area and the at least one detection area comprise a fibrous material.

38. An analytical device as recited in claim 32, wherein at least one sample application area, detection area, and absorbent connector comprise a porous material.

39. An analytical device as recited in claim 32, wherein said layer of flat material has a consistent chemical make-up throughout.

40. An analytical device as recited in claim 32, wherein said sample application area and said detection area are located on a same surface of said layer of flat material.

41. An analytical device for determining an analyte in a liquid sample, said analytical device comprising:

a layer of flat material having at least one absorbent sample application area and at least one absorbent detection area, said at least one absorbent detection area having a reagent for determining the analyte, said absorbent sample application area and said absorbent detection area being disposed within a liquid impermeable boundary, said layer of flat material being formed of a mixture of heat-meltable and non-heat-meltable material, wherein said liquid impermeable boundary comprises heat treated areas of said mixture of heat-meltable and non-heat-meltable material, wherein the heat treatment reduces absorbance of the heat treated areas, wherein said layer of flat material further comprising at least one absorbent connector, said absorbent connector being disposed such that said sample application area and said detection area are connected by said absorbent connector, wherein said liquid impermeable boundary and said absorbent connector prevent liquid from being transported between said at least one sample application area and said at least one detection area, except through said absorbent connector.

42. An analytical device as recited in claim 41, wherein said at least one detection area is a plurality of detection areas, each of said plurality of detection areas being connected to said sample application area by a corresponding plurality of said absorbent connectors.

43. An analytical device as recited in claim 42, wherein said at least one sample application area is a plurality of sample application areas.

44. An analytical device as recited in claim 41, wherein said liquid-impermeable boundary comprises a material which is not a same material as the layer of material comprising the absorbent sample application area and the absorbent detection area.

45. An analytical device as recited in claim 41, wherein a surface area of said at least one sample application area is larger than a surface area of said at least one detection area.

46. An analytical device as recited in claim 41, wherein the at least one sample application area and the at least one detection area comprise a fibrous material.

47. An analytical device as recited in claim 41, wherein at least one sample application area, detection area, and absorbent connector comprise a porous material.

48. An analytical device as recited in claim 41, wherein said layer of flat material has a consistent chemical make-up throughout.

49. An analytical device as recited in claim 41, wherein said sample application area and said detection area are located on a same surface of said layer of flat material.

50. A process for manufacturing an analytical device for determining an analyte in a liquid sample, said process comprising the steps of:

providing a layer of flat absorbent first material;

forming at least one absorbent sample application area on said layer of flat first material;

forming at least one absorbent detection area on said layer of flat first material;

forming at least one absorbent connector connecting said at least one sample application area and said at least one detection area;

providing a heat-deformable second material;

locating said heat-deformable second material under said layer of flat first material, wherein said steps of forming the sample application area, forming the detection area, and forming the absorbent connector are performed by heat-treatment of the heat-deformable second material such that the absorbent flat first material is affected in selected areas so that it is no longer absorbent, wherein said at least one sample application area, said at least one detection area, and said absorbent connector are disposed within a liquid impermeable boundary, said liquid impermeable boundary being formed during said forming steps, and wherein said at least one absorbent detection area includes a reagent for determining the analyte in a liquid sample.

51. A process for manufacturing an analytical device for determining an analyte in a liquid sample, said process comprising the steps of:

providing a layer of flat absorbent first material;

forming at least one absorbent sample application area on said layer of flat first material;

forming at least one absorbent detection area on said layer of flat first material;

forming at least one absorbent connector connecting said at least one sample application area and said at least one detection area, said at least one absorbent connector having a cross-section which is less than a cross-section of the sample application area and a cross-section of the detection area, wherein said at least one sample application area, said at least one detection area, and said absorbent connector are disposed within a liquid impermeable boundary, said liquid impermeable boundary being formed during said forming steps, and wherein said at least one absorbent detection area includes a reagent for determining the analyte in a liquid sample.

52. A process for manufacturing an analytical device as recited in claim 51, wherein said steps of forming said sample application area, forming said detection area, and forming said absorbent connector comprises heat treatment of portions of said layer of flat first material forming the liquid impermeable boundaries.

53. A process for manufacturing an analytical device as recited in claim 52, wherein said heat treatment is performed with ultrasound.

54. A process for manufacturing an analytical device as recited in claim 51, further comprising the steps of:

providing a heat-deformable second material;

locating said heat-deformable second material under said layer of flat first material, wherein said steps of forming the sample application area, forming the detection area, and forming the absorbent connector are performed by heat-treatment of the heat-deformable second material such that the absorbent flat first material is affected in selected areas so that it is no longer absorbent.

55. A process for manufacturing an analytical device for determining an analyte in a liquid sample, said process comprising the steps of:

providing a layer of flat absorbent first material;

forming at least one absorbent sample application area on said layer of flat first material;

forming at least one absorbent detection area on said layer of flat first material;

forming at least one absorbent connector connecting said at least one sample application area and said at least one detection area, wherein said at least one sample application area, said at least one detection area, and said absorbent connector are disposed within a liquid impermeable boundary, said liquid impermeable boundary being formed during said forming steps, and wherein said at least one absorbent detection area includes a reagent for determining the analyte in a liquid sample, said layer of flat absorbent material being a heat-meltable material wherein said liquid-impermeable boundaries comprise heat treated areas of said heat-meltable material, wherein the heat treatment reduces the absorbency of the heat treated areas.

56. A process for manufacturing an analytical device as recited in claim 55, wherein said steps of forming said sample application area, forming said detection area, and forming said absorbent connector comprises heat treatment of portions of said layer of flat first material forming the liquid impermeable boundaries.

57. A process for manufacturing an analytical device as recited in claim 55, further comprising the steps of:
providing a heat-deformable second material;
locating said heat-deformable second material under said layer of flat first material, wherein said steps of forming the sample application area, forming the detection area, and forming the absorbent connector are performed by heat-treatment of the heat-deformable second material such that the absorbent flat first material is affected in selected areas so that it is no longer absorbent.

58. A process for manufacturing an analytical device for determining an analyte in a liquid sample, said process comprising the steps of:
providing a layer of flat absorbent first material;
forming at least one absorbent sample application area on said layer of flat first material;
forming at least one absorbent detection area on said layer of flat first material;
forming at least one absorbent connector connecting said at least one sample application area and said at least one detection area,
wherein said at least one sample application area, said at least one detection area, and said absorbent connector are disposed within a liquid impermeable boundary, said liquid impermeable boundary being formed during said forming steps, and wherein said at least one absorbent detection area includes a reagent for determining the analyte in a liquid sample, and wherein said layer of flat material comprises a mixture of heat-meltable and non-heat-meltable material, wherein said liquid impermeable boundary comprises heat treated areas of said heat-meltable material, wherein the heat treatment reduces absorbance of the heat treated areas.

59. A process for manufacturing an analytical device as recited in claim 58, wherein said steps of forming said sample application area, forming said detection area, and forming said absorbent connector comprises heat treatment of portions of said layer of flat first material forming the liquid impermeable boundaries.

60. A process for manufacturing an analytical device as recited in claim 59, wherein said heat treatment is performed with ultrasound.

61. A process for manufacturing an analytical device as recited in claim 58, further comprising the steps of:
providing a heat-deformable second material;
locating said heat-deformable second material under said layer of flat first material, wherein steps of forming the sample application area, forming the detection area, and forming the absorbent connector are performed by heat-treatment of the heat-deformable second material such that the absorbent flat first material is affected in selected areas so that it is no longer absorbent.

62. An analytical device as recited in claim 1, further comprising absorbent functional areas within said liquid impermeable boundary, said absorbent functional areas interrupting said absorbent connector between said sample application area and said detection area.

63. An analytical device as recited in claim 62, wherein said functional areas have a cross-section which is greater than a cross-section of the absorbent connector.

64. An analytical device as recited in claim 18, further comprising absorbent functional areas within said liquid impermeable boundary, said absorbent functional areas interrupting said absorbent connector between said sample application area and said detection area.

65. An analytical device as recited in claim 64, wherein said functional areas have a cross-section which is greater than a cross-section of the absorbent connector.

66. An analytical device as recited in claim 21, further comprising absorbent functional areas within said liquid impermeable boundary, said absorbent functional areas interrupting said absorbent connector between said sample application area and said detection area.

67. An analytical device as recited in claim 66, wherein said functional areas have a cross-section which is greater than the cross-section of the absorbent connector.

68. An analytical device as recited in claim 32, further comprising absorbent functional areas within said liquid impermeable boundary, said absorbent functional areas interrupting said absorbent connector between said sample application area and said detection area.

69. An analytical device as recited in claim 68, wherein said functional areas have a cross-section which is greater than a cross-section of the absorbent connector.

70. An analytical device as recited in claim 41, further comprising absorbent functional areas within said liquid impermeable boundary, said absorbent functional areas interrupting said absorbent connector between said sample application area and said detection area.

71. An analytical device as recited in claim 70, wherein said functional areas have a cross-section which is greater than a cross-section of the absorbent connector.

72. A process for manufacturing an analytical device as recited in claim 9, further comprising the step of forming at least one absorbent functional area within said liquid impermeable boundary, said absorbent functional area interrupting said absorbent connector between said sample application area and said detection area.

73. A process for manufacturing an analytical device as recited in claim 72, wherein said absorbent functional area is formed with a cross-section which is larger than a cross-section of the absorbent connector.

74. A process for manufacturing an analytical device as recited in claim 12, further comprising the step of forming at least one absorbent functional area within said liquid impermeable boundary, said absorbent functional area interrupting said absorbent connector between said sample application area and said detection area.

75. A process for manufacturing an analytical device as recited in claim 74, wherein said absorbent functional area is formed with a cross-section which is larger than a cross-section of the absorbent connector.

76. A process for manufacturing an analytical device as recited in claim 14, further comprising the step of forming at least one absorbent functional area within said liquid impermeable boundary, said absorbent functional area interrupting said absorbent connector between said sample application area and said detection area.

77. A process for manufacturing an analytical device as recited in claim 76, wherein said absorbent functional area is formed with a cross-section which is larger than a cross-section of the absorbent connector.

78. A process for manufacturing an analytical device as recited in claim 50, further comprising the step of forming at least one absorbent functional area within said liquid impermeable boundary, said absorbent functional area interrupting said absorbent connector between said sample application area and said detection area.

79. A process for manufacturing an analytical device as recited in claim 78, wherein said absorbent functional area is formed with a cross-section which is larger than a cross-section of the absorbent connector.

80. A process for manufacturing an analytical device as recited in claim 51, further comprising the step of forming at least one absorbent functional area within said liquid impermeable boundary, said absorbent functional area interrupting said absorbent connector between said sample application area and said detection area.

81. A process for manufacturing an analytical device as recited in claim 80, wherein said absorbent functional area is formed with a cross-section which is larger than the cross-section of the absorbent connector.

82. A process for manufacturing an analytical device as recited in claim 55, further comprising the step of forming at least one absorbent functional area within said liquid impermeable boundary, said absorbent functional area interrupting said absorbent connector between said sample application area and said detection area.

83. A process for manufacturing an analytical device as recited in claim 82, wherein said absorbent functional area is formed with a cross-section which is larger than a cross-section of the absorbent connector.

84. A process for manufacturing an analytical device as recited in claim 58, further comprising the step of forming at least one absorbent functional area within said liquid impermeable boundary, said absorbent functional area interrupting said absorbent connector between said sample application area and said detection area.

85. A process for manufacturing an analytical device as recited in claim 84, wherein said absorbent functional area is formed with a cross-section which is larger than a cross-section of the absorbent connector.

* * * * *